United States Patent [19]

Fazzini

[11] 4,176,129
[45] Nov. 27, 1979

[54] PROCESS FOR THE PREPARATION OF TRIS(HYDROXYMETHYL)-AMINOME-THAN-LACTATE-DIHYDROXYALUMINATE

[75] Inventor: Massimo Fazzini, Milan, Italy

[73] Assignee: Scharper S.p.A. Per l'Industria Farmaceutica, Italy

[21] Appl. No.: 910,085

[22] Filed: May 26, 1978

[30] Foreign Application Priority Data

Jun. 7, 1977 [IT] Italy ................................ 24428 A/77

[51] Int. Cl.² ................................................. C07F 5/06
[52] U.S. Cl. .......................... 260/448 R; 260/448 AD
[58] Field of Search ..................... 260/448 R, 448 AD

[56] References Cited

U.S. PATENT DOCUMENTS

| | | | |
|---|---|---|---|
| 2,844,551 | 7/1958 | Orthner et al. | 260/448 AD |
| 2,910,494 | 10/1959 | Rinse | 260/448 R |
| 3,267,091 | 8/1966 | Denison | 260/448 R |
| 3,492,329 | 1/1970 | Davison et al. | 260/448 R |
| 4,042,680 | 8/1977 | Muhler et al. | 260/448 R X |

*Primary Examiner*—Helen M. S. Sneed
*Attorney, Agent, or Firm*—McGlew and Tuttle

[57] ABSTRACT

A process for the production of tris(hydroxymethyl)-aminomethan-lactate-dihydroxyaluminate by the reaction of equimolar quantities of lactic acid, tris aminomethane and aluminum isopropylate.

4 Claims, No Drawings

PROCESS FOR THE PREPARATION OF TRIS(HYDROXYMETHYL)-AMINOMETHAN-LACTATE-DIHYDROXYALUMINATE

The present invention relates to a method for producing tris(hydroxymethyl)-aminomethan-lactate dihydroxyaluminate, having an empirical formula of $C_7H_{18}NO_8Al$, a molecular weight of 271.21, and having the following structural formula:

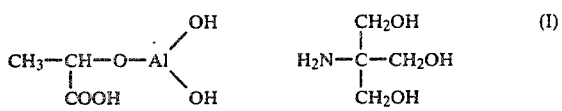

The compound obtained according to the process of the present invention has a very high activity as an antacid, particularly due to its high neutralizing capacity on a weight by weight basis.

The process according to the present invention begins with the solubilization in water of lactic acid and with the subsequent addition of tris-hydroxymethyl aminomethane (THAM) and of aluminum isopropylate, said additions being capable of being effected indifferently in any sequence.

The present invention will be better understood by the following operative examples of the invention given purely by way of illustration and not of limitation.

EXAMPLE 1

In a 1 liter round-bottom flask, equipped with stirrer, reflux condenser and thermometer, there is dissolved 51 g of lactic acid (88%) (0.5 mol) in 300 ml of water.

To this solution there is added portion wise 102 g of aluminum isopropylate (0.5 mol).

There results a fair exothermic reaction which raises the interior temperature of the flask to about 50° C.

The suspension is then heated, with stirring to 60° C. for two hours. It is then cooled to 25° C.

There is thus obtained an opalescent solution to which there is added 60.5 g of THAM (0.5 mol). The mixture is stirred at room temperature for one hour.

The insoluble residue is then removed by filtration and the filtrate is concentrated under reduced pressure to a dry residue, keeping the bath temperature below 50° C.

The solid residue is then dried under reduced pressure to constant weight, at a temperature of 40° C.

There are obtained 133 g of the product of formula (I) that is, tris(hydroxymethyl)-aminomethan-lactate dihydroxyaluminate.

EXAMPLE 2

In a 3 liter round bottom flask, equipped with stirrer, reflux condenser and thermometer, there is dissolved 102 g of lactic acid (88%) (1 mol) in 600 ml of water.

To the flask there is then added 121 g of THAM (1 mol). After a solution is obtained, there is added 204 g of aluminum isopropylate (1 mol) dissolved in 1 liter of isopropyl alcohol.

The mixture is then stirred for 2 hours at room temperature.

The insoluble residue is filtered and the filtrate is concentrated under reduced pressure until a dry residue is obtained.

Said residue is then removed from the flask and dried under reduced pressure in the presence of silica gel to constant weight.

There are obtained 268 g of the product of formula (I) that is, tris(hydroxymethyl)-aminomethan-lactate dihydroxyaluminate.

EXAMPLE 3

In a 10 liter round bottom flask, equipped with stirrer, reflux condenser and thermometer, there is dissolved 510 g of lactic acid (88%) (5 mol) in 3 liters of water.

To the solution there is added 605 g of THAM (5 mol) and the resulting mixture is stirred for 30 minutes at room temperature.

There is then added in small portions 1020 g (5 mol) of aluminum isopropylate.

There is as a result a slight exothermic reaction (to about 35° C.).

The mixture is then heated for a period of 2 hours at 65° C. until an opalescent solution is obtained.

The product is isolated by removing the water by means of a spray-drying apparatus.

There is obtained 1340 g of the product of formula (I), that is tris(hydroxymethyl)-aminomethan-lactate dihydroxyaluminate.

| | | | | ANALYTICAL COMPARATIVE TABLE | | | | | |
|---|---|---|---|---|---|---|---|---|---|
| | | | | ANTACID | ELEMENTAL ANALYSIS | | | | |
| | | | | | C | | H | | N |
| Example No. | % H₂O (KF) | Compl. Titer | PH (5% sol.) | ACTIVITY ml HCl 0.1N | Calc. | Found | Calc. | Found | Calc. | Found |
| 1 | 4.65 | 99.6 | 7.88 | 151 | 31.00 | 30.64 | 6.68 | 6.96 | 5.16 | 4.99 |
| 2 | 2.66 | 98.2 | 8.02 | 149 | 31.00 | 31.21 | 6.68 | 6.59 | 5.16 | 5.07 |
| 3 | 2.05 | 99.1 | 7.91 | 152 | 31.00 | 30.75 | 6.68 | 6.44 | 5.16 | 4.98 |

For a better understanding of the invention there follows a description which illustrates how the antacid activity was determined.

To a water glass having a capacity of 400 ml and maintained into a constant temperature bath of 37° C., there is added 200 ml of 0.015 N HCl.

When the liquid in the glass has reached the bath temperature of 37° C., there is added thereto a quantity of the test sample equivalent to 2.3 g of product, stirring with a glass rod to facilitate the solubilization of the powder. At 30 minutes after the addition of the powder, the pH of the solution is measured, verifying that said pH is between 5.0 and 6.5. There is then added, by means of a 50 ml burette, 0.1 N HCl at the rate of 1 ml per minute, with slight agitation. The determination is considered finished when the pH of the solution has reached 3.0.

While there have been given only few examples of the actuation of the process of the present invention, it is obvious to one skilled in the art that various modifications thereof can be effected without departing from the scope of the present invention and remaining in the ambit thereof.

What is claimed is:

1. A process for the production of tris (hydroxymethyl)-aminomethan-lactate-dihydroxyaluminate which comprises reacting equimolar quantities each of: (a) lactic acid, (b) tris(hydroxymethyl)aminomethane, and (c) aluminum isopropylate.

2. Process as claimed in claim 1, wherein to the lactic acid there is first added aluminum isopropylate, and then the trishydroxymethyl aminomethane reactant is added to the resultant composition.

3. Process as claimed in claim 1, which comprises adding the tris(hydroxymethyl) aminomethane reactant to an aqueous solution of lactic acid and subsequently adding thereto a solution of aluminum isopropylate in isopropyl alcohol.

4. Process as claimed in claim 1, which comprises adding the tris(hydroxymethyl) aminomethane reactant to an aqueous solution of lactic acid and subsequently adding thereto, in small portions, aluminum isopropylate.

* * * * *